(12) United States Patent
Hornack et al.

(10) Patent No.: US 9,808,441 B2
(45) Date of Patent: *Nov. 7, 2017

(54) DIETARY SUPPLEMENT CONTAINING ALKALINE ELECTROLYTE BUFFERS

(71) Applicants: Janmarie Hornack, Overland Park, KS (US); Lawrence E. Dorman, Grain Valley, MO (US)

(72) Inventors: Janmarie Hornack, Overland Park, KS (US); Lawrence E. Dorman, Grain Valley, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 15/165,416

(22) Filed: May 26, 2016

(65) Prior Publication Data

US 2016/0271103 A1 Sep. 22, 2016

Related U.S. Application Data

(60) Division of application No. 14/053,228, filed on Oct. 14, 2013, now Pat. No. 9,357,797, which is a
(Continued)

(51) Int. Cl.

| | |
|---|---|
| *A01N 59/06* | (2006.01) |
| *A61K 31/375* | (2006.01) |
| *A23L 33/16* | (2016.01) |
| *A61K 31/047* | (2006.01) |
| *A61K 31/07* | (2006.01) |
| *A61K 31/10* | (2006.01) |
| *A61K 31/122* | (2006.01) |
| *A61K 31/14* | (2006.01) |
| *A61K 31/145* | (2006.01) |
| *A61K 31/197* | (2006.01) |
| *A61K 31/202* | (2006.01) |
| *A61K 31/205* | (2006.01) |
| *A61K 31/355* | (2006.01) |
| *A61K 31/401* | (2006.01) |
| *A61K 31/4188* | (2006.01) |
| *A61K 31/4415* | (2006.01) |
| *A61K 31/455* | (2006.01) |
| *A61K 31/51* | (2006.01) |
| *A61K 31/519* | (2006.01) |
| *A61K 31/525* | (2006.01) |
| *A61K 31/593* | (2006.01) |
| *A61K 31/7004* | (2006.01) |
| *A61K 31/714* | (2006.01) |
| *A61K 33/00* | (2006.01) |
| *A61K 33/04* | (2006.01) |

(Continued)

(52) U.S. Cl.
CPC .......... *A61K 31/375* (2013.01); *A23L 33/105* (2016.08); *A23L 33/15* (2016.08); *A23L 33/155* (2016.08); *A23L 33/16* (2016.08); *A61K 31/047* (2013.01); *A61K 31/07* (2013.01); *A61K 31/10* (2013.01); *A61K 31/122* (2013.01); *A61K 31/14* (2013.01); *A61K 31/145* (2013.01); *A61K 31/197* (2013.01); *A61K 31/202* (2013.01); *A61K 31/205* (2013.01); *A61K 31/355* (2013.01); *A61K 31/401* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/593* (2013.01); *A61K 31/7004* (2013.01); *A61K 31/714* (2013.01); *A61K 33/00* (2013.01); *A61K 33/04* (2013.01); *A61K 33/06* (2013.01); *A61K 33/10* (2013.01); *A61K 33/30* (2013.01); *A61K 33/32* (2013.01); *A61K 33/34* (2013.01); *A61K 33/42* (2013.01); *A61K 36/03* (2013.01); *A61K 36/16* (2013.01); *A61K 36/185* (2013.01); *A61K 36/258* (2013.01); *A61K 36/30* (2013.01); *A61K 36/734* (2013.01); *A61K 36/738* (2013.01); *A61K 36/752* (2013.01); *A61K 38/05* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,568,547 A | 2/1986 | Herschler | |
| 4,579,843 A | 4/1986 | Ehrenpreis et al. | |

(Continued)

FOREIGN PATENT DOCUMENTS

| | | | |
|---|---|---|---|
| WO | WO 9850051 | * | 11/1998 |
| WO | WO9921437 | | 5/1999 |

OTHER PUBLICATIONS

Winther et al., Inflammopharmacology, 1999, vol. 7, No. 1, p. 63-68.

(Continued)

*Primary Examiner* — Kade Ariani
(74) *Attorney, Agent, or Firm* — Law Office of John C. McMahon

(57) ABSTRACT

An improved dietary and/or therapeutic supplement composition comprising a quantity of a dietary and/or therapeutic supplement agent having a pH that upon ingestion with food or a beverage would limit the effectiveness of the agent and a sufficient amount of an alkaline electrolyte additive is provided in combination with the agent to raise the pH of the composition to a level of from about 8 to about 12.5 to increase the effectiveness and functional utilization of the agent while the composition is in the person's stomach.

13 Claims, No Drawings

Related U.S. Application Data continuation-in-part of application No. 13/694,092, filed on Oct. 30, 2012, now Pat. No. 8,557,299, which is a continuation of application No. 12/082,510, filed on Apr. 11, 2008, now Pat. No. 8,298,588, which is a division of application No. 10/679,535, filed on Oct. 3, 2003, now Pat. No. 7,597,909, which is a continuation of application No. 09/706,005, filed on Nov. 3, 2000, now abandoned.

(60) Provisional application No. 60/164,085, filed on Nov. 6, 1999.

(51) Int. Cl.

| | | |
|---|---|---|
| *A61K 33/06* | (2006.01) | |
| *A61K 33/10* | (2006.01) | |
| *A61K 33/30* | (2006.01) | |
| *A61K 33/32* | (2006.01) | |
| *A61K 33/34* | (2006.01) | |
| *A61K 33/42* | (2006.01) | |
| *A61K 36/03* | (2006.01) | |
| *A61K 36/16* | (2006.01) | |
| *A61K 36/185* | (2006.01) | |
| *A61K 36/258* | (2006.01) | |
| *A61K 36/30* | (2006.01) | |
| *A61K 36/734* | (2006.01) | |
| *A61K 36/738* | (2006.01) | |
| *A61K 36/752* | (2006.01) | |
| *A61K 38/05* | (2006.01) | |
| *A23L 33/105* | (2016.01) | |
| *A23L 33/15* | (2016.01) | |
| *A23L 33/155* | (2016.01) | |

(56) References Cited

U.S. PATENT DOCUMENTS

| | | |
|---|---|---|
| 5,306,511 A | 4/1994 | Whang |
| 5,424,074 A | 6/1995 | Koli et al. |
| 5,455,050 A | 10/1995 | Beyerle et al. |
| 5,849,346 A | 12/1998 | Hornack |
| 5,853,748 A | 12/1998 | New |
| 5,888,514 A | 3/1999 | Weisman |
| 5,914,130 A | 6/1999 | Whang |
| 6,123,944 A | 9/2000 | Chen et al. |
| 6,139,872 A | 10/2000 | Walsh |
| 6,162,787 A | 12/2000 | Sorgente et al. |
| 6,224,871 B1 | 5/2001 | Hastings et al. |
| 6,261,600 B1 | 7/2001 | Kirschner et al. |
| 6,346,519 B1 | 2/2002 | Petrus |
| 7,597,909 B2 | 10/2009 | Hornack et al. |
| 8,298,588 B2 | 10/2012 | Hornack et al. |
| 8,557,299 B2 | 10/2013 | Hornack et al. |
| 2003/0180389 A1 | 9/2003 | Phillips |

OTHER PUBLICATIONS

Overvad et al., European Journal of Clinical Nutrition, 1999, vol. 53, p. 764-770.

\* cited by examiner

DIETARY SUPPLEMENT CONTAINING ALKALINE ELECTROLYTE BUFFERS

CROSS-REFERENCE TO RELATED APPLICATIONS

This application is a divisional of U.S. patent application Ser. No. 14/053,228, filed Oct. 14, 2013. U.S. patent application Ser. No. 14/053,228 is a continuation-in-part of U.S. patent application Ser. No. 13/694,092 filed Oct. 30, 2012, which is a continuation of U.S. application Ser. No. 12/082,510 filed Apr. 11, 2008 and now U.S. Pat. No. 8,298,588. U.S. application Ser. No. 12/082,510 is a division of Ser. No. 10/679,535 filed Oct. 3, 2003 and now U.S. Pat. No. 7,597,909, which is a continuation of U.S. patent application Ser. No. 09/706,005 filed Nov. 3, 2000, and which claims priority from U.S. Provisional Application Ser. No. 60/164,085 filed Nov. 6, 1999 all of which are incorporated into the present application by reference thereto.

BACKGROUND OF THE INVENTION

The present invention relates to dietary or therapeutic supplements for improving a person's health and well-being, and to a method for neutralizing deleterious acid conditions that occur when a person ingests foods and beverages in conjunction with therapeutic dietary supplements. As a result, an excessive acid condition in the person's stomach that could interfere with the beneficial effect of the food or beverage is avoided. Dietary and therapeutic supplements such as herbs, and certain compounds known to promote health and well-being are utilized more efficiently in an alkaline environment.

It has been widely accepted that dietary therapeutic supplements are recommended for a variety of the healing properties and for boosting the body's natural abilities to react to disease and protect the body's natural function. It has also been widely accepted that the body functions better with a preferred pH in various systems within the body, such as blood stream, stomach, various organs, skin, etc. The ability of the body to properly digest and utilize various nutrients from food, beverages or from dietary supplements, is directly related to the pH of the body and its various systems.

Many dietary and therapeutic supplements contain directions that they should be taken with a meal. In fact, most doctors, such as those caring for women who might be pregnant, when prescribing such supplements, indicate to the patients that the supplement should be taken with meals. Even when supplements and medicines are taken on an empty stomach with a beverage, the ability to digest and adsorb are normally dependent upon pH stability.

Literature references such as Reverse Aging (Sang Whang), Alkalize or Die (Dr. Theodore Baroody) and Acid and Alkaline (Herman Aihara), indicate that most of the food and beverages ingested at meals generate an acid pH in the body. The body then attempts to counteract acidic conditions by releasing alkaline buffers stored in the body to neutralize pH in the body's various systems to a "normal" range for that system, i.e. blood, stomach, urine, colon, pancreas, adrenals etc. Additionally, the body utilizes any alkaline pH nutrient that is ingested with the meal to balance the pH. However, the naturally occurring buffers in the body are normally inadequate to assure that the utilization environment of the supplement in an individual's body is sufficiently alkaline to protect the active agent of the supplement.

There is a large consumer market for products that include, for example, calcium carbonate and/or magnesium oxide to aid in counteracting the acid pH that results from digestion of foods and beverages, thus causing acid toxic waste in a person's body. Additionally, devices have been provided for consumer use such as machines that produce alkaline water to offset these acid conditions and products have been created to reduce acidity (such as Acid pHree™).

In the Whang (U.S. Pat. Nos. 5,306,511 and 5,914,130), the patentee states that the elimination of acid wastes from the body is greatly enhanced through the use of alkaline water and alkaline minerals in the form of sodium and potassium bicarbonate. Additionally, the compositions are indicated to prevent increased acidity in various systems of the body through the use of blood buffers and to aid the body's pH control system from experiencing extreme fluctuations in the pH value. The acid waste is believed by many in the medial community to be the primary or a major contributing factor in certain adult degenerative states in the body such as diabetes and kidney disease.

Whang further asserts in the '511 and '130 patents that by maintaining a blood buffer, and resisting changes in hydrogen ion concentrations, a positive effect is realized by balance and stabilization of the pH in the body. Whang also indicates that it is not only the amount of minerals taken that is a factor, but also the mating or interaction between the minerals that is significant.

In the Hornack U.S. Pat. No. 5,849,346, patentee discloses an additive for beverages which includes potassium hydroxide and a mixture of electrolyte ions such as the alkaline minerals (sodium, potassium, calcium and magnesium) in various forms (hydroxides, chlorides, carbonates, gluconates, bicarbonates, phosphates, sulfates, chelates, diphosphates, oxides and stearates). Hornack's additive is said to be useful for increasing the normally acidic pH of the beverage to a value from 9.5 to as much as 14.0 in beverages.

SUMMARY OF THE INVENTION

The present invention relates to a dietary and/or therapeutic supplement composition for promoting a person's health and well-being, and to a method of enhancing the utilization of such supplements by incorporation of a sufficient quantity of alkaline buffering agents in the supplement to increase the ability of the body to more readily accept and utilize all of the supplement healing agents at a more absorbable level. This invention may be utilized in tablet, capsule, powder or liquid forms. A preferred supplement formulation is a non liquid tablet form, although essentially equivalent results may be obtained with a liquid supplement.

The improved dietary and/or therapeutic supplement composition of the present invention comprises a combination of a supplement that promotes health and well-being in conjunction with alkaline minerals and/or electrolytes which function as buffers upon ingestion of the supplement, particularly when the supplement is taken at mealtime. The improved supplement composition stabilizes the pH ranges in the person's body to acceptable levels, and minimizes pH fluctuations in the user's stomach, particularly when the supplements are taken at mealtime, so that supplements or medicaments may be utilized appropriately at optimum levels, especially by raising the pH of ingested material and body fluid pH levels. The additives for the supplement composition are combinable with supplements of choice which address the preventative or healing task required. The improved supplement composition hereof further may include appropriate amounts of vitamins in various forms, as for example, Vitamin C, which effectively aid the body in the utilization of certain dietary supplements. There is mounting evidence that supplements which are ingested in combination with Vitamin C provides better patient results.

The present invention comprises an improved dietary and/or therapeutic supplement composition in combination, a quantity of a dietary and/or therapeutic supplement agent wherein the agent has a pH that upon ingestion would limit the effectiveness of the agent, and a sufficient amount of an electrolyte additive in combination with the agent to raise the pH of the combination to a level of at least about 8 to increase the effectiveness of the agent upon ingestion of the composition. It is noted that wherein pH is referred to for a dry or non-liquid material, it means where the material is mixed with a liquid, such as in the body of a user.

It is desirable to provide a composition, preferably a dry composition, and method of enhancing the functionality of dietary supplements for optimum utilization of the supplement agent(s) by the various systems of the body.

It is also desirable to provide a composition which assists in developing a more alkaline environment inside the body for enhancement of the excretion of waste of acidic compounds.

It is also desirable to provide a better environment for supplement agents during the digestion process and for the movement of dietary supplements throughout the body. The alkaline electrolytes added to the supplement are preferably one or more of the four electrolytes normally present in the body and that enable fluid to move extracellular, intercellular and intracellular.

Under the invention of the present application, a number of desirable dietary and/or therapeutic supplement agents are preferably combined with alkaline buffers that are present in respective proper ratios as required by the body to permit most effective utilization of the supplement, so that a person can buy the combined supplement composition and need not buy several separate bottles of supplements to achieve the same goal.

It is also desirable for certain embodiments of the invention to provide a supplement composition that creates a better pH range overall in the body, so that the body is not losing buffering agents at an undesirable rapid pace, thus aiding the body in decreasing the degree and rate of the aging and disease processes.

DETAILED DESCRIPTION OF THE INVENTION

The present invention provides an improved supplement composition and method for improving the utilization by a person of supplements which promote healing and well-being of a person upon ingestion of the supplement composition. Moreover, the invention supplies electrolyte buffers that are essential for health (preferably one to four alkaline minerals, all of which are electrolytes required for functioning of the body).

The supplement composition of the present invention is operable to enhance stabilization of pH in the person's body, to decrease fluctuations of pH in a person's system, to reduce acid toxic waste, and to improve the balance and level of alkaline minerals and increase the buffering capabilities of electrolytes.

There is evidence that the ability of a therapeutic supplement such as methylsulfonylmethane ("MSM") to properly and efficiently function as expected is reduced by an acid pH in the person's digestive system, so as to have an adverse effect on the functionality of the MSM. Also, it has been established that the body requires alkaline minerals to perform functions in addition to the raising of pH and the buffering of acidic compositions in the body. For example, it is known that calcium is required for rebuilding bone mass and that a lack of usable calcium may result in disease such as osteoporosis. A less known, but nevertheless important fact, is that magnesium is required by the body to properly utilize the calcium and to aid in the prevention of heart attacks. The initiative in this area of study has been done by Paul Mason of Patterson, Calif. The National Academy of Sciences (NAS) is conducting a study for the FDA on the dietary benefits of calcium and magnesium. Mr. Mason has asserted that there is a global pattern of disease from a deficiency in magnesium. Research at the California Department of Health Services has suggested that the addition of 10 ml to 30 mg/liter of magnesium to water per day may account for a significant drop that is being experienced demographically in the rate of heart disease. It is also well known that alkaline minerals are required by the body in amounts that are not normally ingested from an individual's normal diet. Sodium is the exception, as many Americans ingest more sodium in their daily food than required, due to increasingly high intake of processed foods and restaurant food.

When a therapeutic supplement is needed for preventive and healing properties and the supplement is taken with a meal (as often indicated by the directions for that supplement from the healing practitioner, or by habit), the body must first be able to:

A. Digest the food and beverage;
B. Buffer the acidic pH;
C. Carry and potentiate the supplement throughout the body; and
D. Retain potency of the supplement to be utilized for its intended purpose, rather then the supplement itself being used by the body as a buffering agent first.

The constituency, amount and relative ratios of supplements to provide a desired therapeutic effect, and the form in which the supplements are taken may vary, often depending upon the minimum level of RDA (recommended daily allowance) for at least certain of the supplements, as well as the nature of the condition being alleviated by the substance. Thus, in providing an optimal pH balance in the person's body, upon ingestion of supplements and the like, the pH of the supplement or medicament itself and the balance required by the body (Guyton, Textbook of Medical Physiology, and Hornack) must be taken into account.

Thus, an agent is provided to be added to a supplement (or medicament) to assure that the supplement meets the goals of the supplement in an alkaline environment in the body. In producing tablets, capsules, powders or liquids containing a therapeutic supplement that is useful for preventive or health improvement, the pH of the supplement or medicament itself must be considered first. Next, the pH value that is ideal for ingestion of the supplement or medicament at the mealtime must be taken into account. To that end, appropriate alkaline electrolytes by weight are added to the supplement agent as are required to provide an ideal pH in the person's stomach upon ingestion of the supplement with the meal or other food or drink. The pH should always be 8.0 or higher when the supplement composition is ingested along with food or drink. The ideal range in the stomach is 8.0 to 10.5, but may go as high as 12.5, depending upon the nature of the supplement or medicine.

No change is made to the supplements themselves; the supplement agent(s) are combined with the requisite alkaline electrolytes in proper ratios to manage factors A, B and D above. In order to improve the ability of the body to move the supplement through the blood stream, many companies practicing the art, have combined their supplements with Vitamin C in various forms, which is known to act as an oxidizing agent and to aid in moving the various nutrients throughout the bloodstream by increasing the oxygen. Studies indicate that use of Vitamin C in combination with supplements aids in increased promotion of healing. Research was published in this area by Linus Pauling, winner of the Nobel Prize for chemistry and recipient of other major scientific honors. The companies that have not included Vitamin C in their formulas, many times suggest or indicate that taking Vitamin C in conjunction with their supplement is recommended, and research on the subject supports this theory. Research also indicates that the use of bioflavonoids potentiate and protect the Vitamin C adsorption. The way that bioflavonoids increase the effectiveness of Vitamin C is believed to be the way in which they act to restore oxidized Vitamin C by working with glutathione.

Regarding the other 3 items (A, B and D), very little attention has previously been given to these matters.

Although sodium can be incorporated in the formulation as one of the electrolytes, it is not preferred because most individuals already exceed their need for sodium in the diet on a daily basis, which can contribute to hypertension. The present invention, while allowing for use of all of the electrolytes to boost pH in conjunction with other supplements, preferably contains calcium, magnesium and potassium, as these tend to be lacking in the diets of many people.

By combining one of the alkaline electrolytes (potassium, calcium, magnesium, and sodium) in the mix of the dietary and/or therapeutic supplement, the body utilizes the electrolyte component(s) to balance acidity and eliminate toxic waste, thereby allowing the nutrient or supplement to be fully utilized for its intended objective. Movement of the dietary supplement is also improved by the provision of the electrolytes: intracellular, intercellular and extracellular. This further contributes to the increased utilization of the dietary supplement.

There are many therapeutic supplements that benefit from the present invention. Two exemplary supplements are glucosamine and MSM (methylsulfonylmethane).

Glucosamine is naturally occurring as a mucopolysaccharide in the body and is required to produce chondroitin. Found in the body in synovial fluid (which lubricates joints), glucosamines are subunits of glucosamino glycans (GAG's). These are synthesized from glutamine and carbohydrate. Amino acids must be replaced in the diet or by a dietary supplement, to stimulate the body's production of hyaluronic acids (HA's). These products have analgesic effects and promote the anabolic behavior in chrondrocytes. With diseases of age, the HA concentration tends to become depleted and replacement with glucosamine is believed to aid in long term repair. It has been suggested that glucosamine functions to build ligaments, increase fluid in the joints, and improve heart valves, tendons, eyes, nails, skin, digestive tract membranes and bone.

Chondroitin sulfates are commonly combined with glucosamines because of a perceived synergistic effect obtained with the combination. The pH range for this type of combined supplement is typically around 3.34 to about 3.39. Upon ingestion of the glucosamine/chondroitin formulation, the body immediately seeks to adjust the pH balance, resulting in depletion in electrolytes from the user's system, causing production of waste, and elimination of a portion of the therapeutic supplement.

Combining glucosamine/chondroitin with designed amounts of less expensive, high pH electrolyte minerals in accordance with the present invention, aids in balancing the pH in the body without depletion of intracellular and extracellular electrolytes from the body and serves to enhance elimination of acid toxic waste. The alkaline material buffers these acids, so that the glucosamine may benefit the problem of the body with the rapid movement of the supplement into all cell structures of the body (intracellular, extracellular and intercellular). The same is true for chondroitin sulfates, which are, in the practice of the art, commonly tableted with the glucosamine. The pH range for this type of combined supplement is typically around 3.34-3.39. If the alkaline electrolytes (agents of the invention) are not incorporated with the supplement and are taken separately from the supplement, the body will immediately release the intra and extracellular buffers, causing more waste, and the elimination of a portion of the supplement with the waste. That is, it is important that the agent and the supplement be taken together and that the agent be adjusted to function optimally with the particular supplement being taken.

Additionally, glucosamine and chondroitin supplements are administered for their ability to decrease pain in joints, which for example results from arthritic conditions (U.S. Pat. No. 5,840,715, Florio). When a combination of glucosamine and chondroitin is taken along with food or beverage as directed, the resulting increase in body acid due to pH value of foods and beverages, has an adverse effect on the effectiveness of the active ingredient supplement. This increase in body acid has another deleterious effect in that it also tends to cause additional deposits of toxins in the very areas of the body which are susceptible to arthritic conditions. This is because the acids are being neutralized by the body's buffer system that produces salts or other waste, much of which is harmful or toxic and must be discarded by the body. The glucosamine and chondroitin, which were administered to relieve the arthritic symptoms, are not as effective and the toxins being generated which tend to deposit in the body's weakest areas are adding to the problem (Whang and Aihara). Therefore, an added benefit is obtained by combining alkaline minerals with an active ingredient such as glucosamine and chondroitin because of the buffering action of the alkaline minerals which results in a part of the acidic deposit eventually begin to clear as the body self corrects its pH in the area.

Furthermore, by combining the relatively high pH alkaline electrolytes with the dietary and/or therapeutic supplement, the body pH is immediately stabilized and the supplement is moved through the system with the electrolytes for balancing and the movement of body fluids. Utilization of the supplement is at a much higher rate than would otherwise be the case if the formulation of the invention had been used.

Another example of the benefits of this invention is in connection with the therapeutic supplement MSM (methylsulfonylmethane). MSM is an organic sulfur, generally found in a pH range of 7.2 to 7.4. In the body, sulfur is the fourth most prevalent mineral. The presence of sulfur in the body appears to be reduced during the aging process. At maturity, the levels of MSM found in the hormonal fluid may be as low as 0.5 ppm. In U.S. Pat. Nos. 4,514,421, 4,559,329, 4,568,547, 4,973,605, and 5,071,878, Herschler has claimed that a level of at least 1.0 ppm be maintained for health and effective immune system. The skin, bones and muscles of the body contain about ½ of the sulfur found in the total body. Sulfur is needed for producing collagen. Herschler states that there is evidence of the benefits of MSM for various health related conditions for animals and man. These include but are not limited to: human tissue pliancy; tumor control; formation of disulfide bonds for connective tissue integrity; repair and restoration of damaged tissue; aid in reducing reaction to allergens; aid in relieving constipation; improving condition of arthritic patients; relieving cramping and sores; reducing hypertension; and many other benefits. Other literature sources indicate that sulfur is required for the creation of new cells, repair of tissue, cartilage, and organs and is found as a component in the blood.

Herschler and other sources indicate that studies were performed with MSM alone compared with MSM plus Vitamin C. Patients taking the combination responded more quickly to treatment. Herschler also presented information indicating that the sulfur present in the food stuffs are highly volatile and processing or cooking effect the availability for the body in order to replace the sulfur, MSM is a preferred embodiment for use in the body.

Dr. S. W. Jacob, in Am. Acad. Meri. Pred., 1983, the current status of MSM medicine has recommended to control hyperacidity and heartburn. Jacob's recommendation is 3000-mg per day. Because MSM is relatively expensive, it is not a practical antacid.

When MSM, taken as a dietary supplement, is combined with the alkaline electrolytes as an agent of this invention in proper ratios for use by the body, the pH of the tablet, powder, capsule or liquid is increased substantially. A preferred MSM tablet formulation in accordance with the present invention is:

In each of two tablets: 1000-mg MSM (standard recommended dose—although ranges are given for body weight), 780-mg Ascorbic Acid (Vitamin C) & 20-mg Bioflavonoid (Vitamin P, to potentiate Vitamin C), 100-mg Calcium Carbonate, 50-mg Potassium Gluconate, and 50-mg Magnesium Oxide, with appropriate binders and coatings, which are well known to those skilled in the art of tableting.

In the example above, the pH of the tablet is significantly increased. In addition, a recommended dose of Vitamin C for this particular supplement is provided. Normally the pH of the ascorbic acid is about 3.23 and the pH of the MSM about 7.2. Thus, a necessary element or agent which aids in rapid promotion of healing is included in the formulation and at the same time the pH of the tablet is increased to about 8.63 by incorporation of required electrolyte constituents in proper ratios. This is a preferred pH range for the combined supplement and electrolyte composition to be taken prior to mealtime to counteract the acid wastes in the digestion process and falls within the range for a better utilization of the supplements. In certain instances, it may be desirable to increase the pH to an even higher value by adding a greater amount of respective alkaline minerals (agent) as described above, or by utilizing other forms of these minerals, such as hydroxides, sulfates, carbonates, bicarbonates, gluconates, oxides, stearates, chelates, di-phosphates, chlorides and phosphates.

In the MSM example above, the pH has ben substantially increased and the synergistic agent of Bioflavonoids has been included to potentiate Vitamin C and so this is a synergistic factor to increase bioavailability when combined with the concept that the alkaline electrolyte increases the bioavailability in the body.

In the MSM example above, the pH has been substantially increased to prevent extreme fluctuation of the pH in the body at mealtime, thus enabling the MSM to be more efficiently utilized by the body to perform the task/tasks for which the supplement is targeted. With the present invention, hyperacidity/heartburn as discussed by Dr. Jacob is managed, and the more expensive MSM supplement is allowed to fully target other problems without partially being used to adjust pH. Since the pH of MSM is typically lower than the pH of the four alkaline mineral additives in any form, a smaller quantity of the alkaline minerals are required to accomplish the same goal of controlling hyperacidity at a much lower cost because of the differential in price of MSM and alkaline mineral additives.

In a study of patients taking pure MSM for therapeutic relief of arthritic conditions it was found that by administering the MSM in the formulation described above, the amount of the MSM required to obtain relief was cut in half over those patients taking pure MSM.

In another formulation, glucosamine and MSM are combined for their respective healing properties and pain relief. Additional supplements known for pain and joint relief are included, such as *Boswellia* extract, dl-phenylalaine, ginseng extract, ginkgo biloba extract and borage powder.

A preferred MSM-Glucosamine Capsule Formula is: 500-mg glucosamine sulfate, 900-mg MSM, 20-mg 20% *Boswellia* extract, 100-mg dl-phenylalanine, 60-mg ascorbic acid, 5-mg citrus bioflavonoids, 50-mg magnesium carbonate, 50-mg potassium carbonate, 100-mg calcium gluconate, 10-mg 5:1 ginseng extract, 10-mg 24% ginkgo biloba, 15-mg pyroxdine hydrochloride and 180-mg 10% gla borage powder.

In the above formulation, the constituent ingredients that minimize and relieve pain are combined with the ascorbic acid, biflavonoids and pyroxdine hydrochloride (synergistic constituents) and are measured for combined pH, the value obtained is 3.75. When the alkaline constituents are added to the active ingredients, the pH value is increased to 8.0 or more. This allows the body to counteract the negative effects of acid toxins thus decreasing body acid neutralization waste and allowing the active constituents to be more fully utilized and for the available supplement to fall within the optimal therapeutic range.

Other kinds of dietary or therapeutic supplements can be utilized at greater levels by the body if the body's pH balance is stabilized in the appropriate pH ranges, and this can occur even at mealtime when the supplements are ingested by utilizing in accordance with the improved supplement composition of the present invention. In many respects, the actual pH of the supplement or medicine is not the controlling issue, other than that the electrolyte additives shift the pH range substantially upwards to facilitate the movement of the supplement and aid the body in the ability to more fully utilize the supplement. Some of these supplements include, but are not limited to: vitamins such as B3, B complex, B12, C, niacin and the like; minerals and trace minerals zinc, copper, boron and similar elements; enzymes such as pepsin, CoEnzyme Q10 and others; amino acids such as L-Taurine, L-Lysine and more; whole food products containing phytonutrients used as dietary supplement, such as the "Complete Fruit and Vegetable Formula" of HealingMD, Inc., Sherman Oaks, Calif.; herbs and herbal extracts; beneficial bacterial and yeast products for replication in the intestinal tract such as *lactobacillus acidophilus*; and mixed dietary and therapeutic supplements and other nutrient products such as mixtures of the above listed constituent ingredients.

In the prior example above, the preferred synergistic ingredients to improve the bioavailability of the therapeutic elements of glucosamine and *Boswellia* extract are: dl-phenylalanine (precursor of tryptophan and serotonin—and amino acid); citrus bioflavonoid as a phytonutrient; genseng extract and ginko biloba as phytonutrients and phytosterols; and borage as an essential fatty acid.

Certain medicaments may also be improved through the use of these electrolytes, particularly when the movement of the therapeutic agent throughout the body quickly is a desirable attribute.

Examples of the pH of dietary or therapeutic supplements prior to combination with required amounts of useful alkaline minerals are set forth in the table below. When an individual takes any one of these supplements with the meal, the body begins the digestion process of the supplement and the meal and the body begins to try to eliminate resulting waste due to needed raise in pH and to buffer the system. The body will utilize any buffer that can be found within the food, supplement, and after that will begin to draw the alkaline minerals from within the system itself. Therefore, by providing the alkaline buffer in combination with the dietary or therapeutic supplement, substantially all of the supplement is retained intact, to aid in healing, for preventive medicine, to assist in the digestion and elimination process and to slow down the problems associated with acid pH, as described by Hornack, Whang, Baroody and Aihara.

The of pH of exemplary of dietary and/or therapeutic supplements are presented in the table below.

| Dietary Supplement | pH |
| --- | --- |
| B Complex | 7.2 |
| Ascorbic Acid | 3.23 |
| Soy Lecithin | 6.8 |
| Emu Oil | 6.5 |
| Zinc | 3.5 |
| St. John's Wart | 4.9 |
| Slippery Elm Bark | 4.1 |
| Glucosamine | 5.5 |
| Gingko Bilboa Leaf Extract | 5.1 |
| Niacin | 3.4 |
| Vitamin E | 6.1 |
| Multivitamins | 5.0-6.0 |

The pH ranges of the alkaline minerals that are preferably included as a part of a dietary or therapeutic supplement composition in the method of the present invention are from 7.2 to 14.0. These include potassium (pH 9.69 and up depending upon the form of potassium); magnesium (7.20 and up depending upon the form of magnesium); and calcium (8.28 and up depending upon the form of calcium). Although sodium is not included in the preferred formulation because most people in the United States already have too much sodium in their diets, sodium as an electrolyte may be included in the supplement composition in those instances where certain individuals need more sodium. For example, for those in need of supplemental sodium beyond what is available in their normal diet, or for athletes who may require more sodium, then a sodium electrolyte can be incorporated in the dietary and/or therapeutic supplement composition as an additional component to raise the pH of the composition. An example of sodium used by athletes for adding immediate electrolytes, moving fluids, and aiding in reducing lactic acid is Gatorade™.

The pH range preferred (8.0-12.5) can be obtained by using the above minerals in any of the forms available that are approved for pharmaceutical, food grade or potable use. Depending upon the combination of supplements in a tablet, capsule, liquid or powder formula, the amount of the alkaline minerals and the form of the alkaline minerals may be adjusted as required.

Preferred embodiments of combinations of electrolytes in accordance with the present invention, include but are not limited to the following ratios of Ca to Mg to K (Ca/Mg/K), on a weight to weight basis: 2/1/1; 2/1/1.5; 2/1/2; 1/0.5/1; 1/0.75/1; 2/0.75/2; 2/1.25/2; 1/0.5/0.5; 2/0.75/0.75 and 2/1.25/0.75.

The amount of magnesium should equal at least 30% to 100% of the calcium. Since there are many calcium supplements on the market today that do not include magnesium, the present invention in that instance boosts the ratio of the Mg/Ca, thus aiding in the proper digestion of Ca ingested in other supplements or in the calcium fortified food products.

The amount of potassium electrolyte levels can vary, depending on the supplement that is combined with the potassium additive. Providing a substantial dose of potassium in the formulation assists in counteracting the effects of too much sodium in a person's body, by providing a proper balance of the two elements.

The mineral electrolyte additive or the dietary and/or therapeutic supplement transport as electrolytes throughout the body, giving the increased advantage of easily moving the digested supplements or medicaments along extracellular, intracellular and intercellular paths.

A preferred liquid composition making up 30-ml aliquot is prepared by admixing: 420-ml of 45% KOH; 10.25-ml $P_2O_5$ (Glass H—a long chain linear polyphosphate) into 200-ml D/I $H_2O$; 1.2-ml NaCl into 125-ml D/I $H_2O$; 1.2-mg CaCl into 100-ml D/I $H_2O$; 3.0-$MgSO_4$ into 150-ml D/I $H_2O$; 3.5-mg $NaHCO_3$ into 100-ml D/I $H_2O$; 0.05-mg bioflavonoid; and 3.0-mg methylsulfonylmethane, and then bringing the solution up to 3750 ml total with D/I $H_2O$.

In certain instances, it may also be desirable to include 0.01 mg of ascorbic acid in the above formulation.

In addition to increasing uptake in a dry dietary supplement, especially in the jejunum and the ileum of the intestine, using alkaline electrolytes (agents), vitamins, minerals and supplements will absorb at a higher amount in the intestine when paired with herbs, herbal extracts, amino acids, phytosterols, phytonutrients, co-enzymes, enzymes, and essential fatty acids as synergistic factors for bioavailability when still utilizing in concept in conjunction with the claims above.

In another formulation, enough alkaline electrolytes (agent) is added to support synergistic factors to further improve bioavailability. Included are supplements such as astaxanthin, hawthorne berry, vitamins, co-enzymes, essential fatty acids and horse chestnut support circulatory and heart function.

The following is an example of a highly beneficial combination of at least one agent and at least one supplement (medicant) in accordance with the invention.

| Ingredient | Quantity |
| --- | --- |
| Vitamin A as Beta-carotene | 500 IU |
| Vitamin B1 (Thiamine) | 4 mg |
| Vitamin B2 (Riboflavin) | 4 mg |
| Vitamin B3 (Nicotinate) | 5 mg |
| Vitamin B5 (Pantothenate) | 5 mg |
| Vitamin B6 (Pyridoxine) | 5 mg |
| Vitamin B12 (Cyanocobalamin) | 10 mcg |
| Vitamin D3 | 1000 IU |
| Vitamin E (d-alpha-Tocopherol) | 60 IU |
| Folic Acid | 400 mcg |
| Biotin | 10 mcg |
| Inositol | 10 mg |
| Calcium Carbonate | 700 mg |
| Magnesium (as Mg-chelate) | 350 mg |

| Ingredient | Quantity |
| --- | --- |
| Potassium | 30 mg |
| Phosphate | 90 mg |
| Zinc | 1 mg |
| Manganese | 1 mg |
| Copper | 70 mcg |
| Selenium | 10 mcg |
| Amino Acid Blend (taurine, L-proline, L-carnitine, L-carnosine) | 500 mg |
| Special Support Blend (Glucosamine, choline, chondroitin bioflavonoids, MSM, kelp, ginseng, gingko biloba extract, fruit blend, rose hips, acerola) | 500 mg |

The following heart and circulation support formula is also a beneficial formulation of at least one supplement in accordance with the invention which is used in conjunction with an alkaline electrolyte especially a potassium, calcium, sodium and/or magnesium electrolyte used to adjust the pH when ingested into the body to at least 8.5.

| Ingredient | Quantity |
| --- | --- |
| Hawthorne berry 8:1 extract | 30 mg |
| Astaxanthin (*Haematococcus pluvailis*) extract | 10 mg |
| Coenzyme Q-10 | 10 mg |
| Borage extract | 50 mg |
| DHA/EPA | 30 mg |

In the prior example above, the synergistic ingredients to improve the bioavailability of the heart and circulation support ingredients are: amino acids, essential fatty acids, minerals and vitamins, herbs and herbal extracts, whole foods, phytonutrients, phytosterols, herbs and their extracts, bioflavonoid used along with an agent comprising an alkaline electrolytes.

It is clear that the present invention is well adapted provide improved efficiency of supplements and to obtain the ends and advantages mentioned as well as those inherent therein. While presently preferred embodiments of the invention have been described for the purposes of this disclosure, it will be recognized that numerous changes may be made which will readily suggest themselves to those skilled in the art and which are encompassed within the spirit of the invention disclosed.

What is claimed and desired to be secured by Letters Patent is as follows:

1. A method of improving uptake of a dry dietary supplement comprising:
    a) providing the supplement in a dry form;
    b) providing an alkaline electrolyte agent comprising electrolytes selected from the group consisting of magnesium, calcium, potassium, sodium electrolytes and mixes thereof in a dry form;
    c) mixing the supplement and agent to from a dry mixture, wherein the agent is provided in sufficient amount such that when mixed with a desired quantity of the supplement the pH of the resulting mixture is in the range from greater than 8 to 12.5, and
    d) feeding the mixture to a person in a dry form.

2. The method according to claim 1 wherein the supplement is selected from the group consisting of Vitamins A, B1, B2, B3, B5, B6, B12, D3, E, folic acid, biotin, inositol, phosphate, zinc, manganese, copper, selenium, amino acids, glucosamine, choline, chondroitin, bioflavonoids, methylsulfonylmethane, kelp, ginseng, gingko biloba extract, rose hips, acerola and mixes thereof.

3. The method according to claim 1 wherein the supplement is selected from the group consisting of hawthorne berry extract, astaxanthin extract, coenzyme Q-10, borage extract, DHA/EPA (docosahexaenoic acid/eicosapentaenoic acid and mixes thereof.

4. The method according to claim 1 wherein the supplement is ascorbic acid.

5. The method according to claim 4 adding the electrolytes as a mixture of calcium, magnesium and potassium.

6. The method according to claim 5 wherein the ratio by weight of calcium to magnesium to phosphorous is about 2/1.25/0.075.

7. The method according to claim 1 including an additional step of adding a citrus bioflavonoid to the mixture.

8. The method according to claim 7 including an additional step of adding rose hips to the mixture.

9. A method of improving uptake of a dry dietary supplement comprising:
    a) providing the supplement comprising vitamin C, bioflavonoid and rose hips in a dry form;
    b) providing an alkaline electrolyte agent comprising electrolytes selected from the group consisting of magnesium, calcium, potassium, sodium electrolytes and mixes thereof in a dry form;
    c) mixing the supplement and agent to from a mixture in a dry form, wherein the agent is provided in sufficient amount such that when mixed with a desired quantity of the supplement the pH of the resulting mixture is in the range from 8 to 12.5, and
    d) feeding the mixture to a person.

10. A method of improving uptake of a dry dietary vitamin C:
    a) providing the vitamin C in a dry form;
    b) providing an alkaline electrolyte agent comprising electrolytes selected from the group consisting of magnesium, calcium, potassium, sodium electrolytes and mixes thereof in a dry form;
    c) mixing the vitamin C and agent to from a dry mixture, wherein the agent is provided in sufficient amount such that when mixed with a desired quantity of vitamin C, the pH of the resulting mixture is in the range from greater than 8 to 12.5, and
    d) feeding the mixture to a person in a dry form.

11. A method of improving uptake of a dry dietary supplement comprising vitamin C, rose hips and bioflavonoid:
    a) providing the supplement comprising vitamin C, rose hips and bioflavonoid in a dry form;
    b) providing an alkaline electrolyte agent in a dry form comprising electrolytes selected from the group consisting of magnesium, calcium, potassium, sodium electrolytes and mixes thereof;
    c) mixing the supplement and agent to from a mixture in a dry form, wherein the agent is provided in sufficient amount such that when mixed with a desired quantity of the supplement, the pH of the resulting mixture is in the range from 8 to 12.5, and
    d) feeding the mixture in a dry form to a person.

12. The method according to claim 1 wherein the supplement is a fruit blend.

13. The method according to claim 9 wherein vitamin C, bioflavonoid, and rose hips are included in a ratio of approximately 500 milligrams of vitamin C to 80 milligrams of bioflavonoid to 20 milligrams of rose hips.

* * * * *